(12) United States Patent
Mamidi et al.

(10) Patent No.: US 6,693,173 B2
(45) Date of Patent: Feb. 17, 2004

(54) METHOD TO REMOVE CITRATE AND ALUMINUM FROM PROTEINS

(75) Inventors: Raja R. Mamidi, Pomona, CA (US); Leticia R. Regis, Lakewood, CA (US); Mauro C. Mojica, Chino Hills, CA (US); Hirokazu Ito, Arcadia, CA (US); Takashi Goto, Arcadia, CA (US)

(73) Assignee: Alpha Therapeutic Corporation, Los Angeles, CA (US)

( * ) Notice: Subject to any disclaimer, the term of this patent is extended or adjusted under 35 U.S.C. 154(b) by 81 days.

(21) Appl. No.: 09/805,397

(22) Filed: Mar. 13, 2001

(65) Prior Publication Data

US 2002/0132985 A1 Sep. 19, 2002

Related U.S. Application Data

(63) Continuation-in-part of application No. 09/752,138, filed on Dec. 26, 2000, now abandoned.

(51) Int. Cl.[7] .................. A61K 35/14; A61K 38/00; A61K 38/48; C07K 16/00
(52) U.S. Cl. .................. 530/364; 530/380; 530/381; 530/382; 530/383; 530/384; 530/387.1; 530/362; 530/363; 530/364; 530/416; 514/12
(58) Field of Search .................. 530/380, 381, 530/382, 383, 384, 387.1, 362, 336, 364, 416; 514/12

(56) References Cited

U.S. PATENT DOCUMENTS

| | | |
|---|---|---|
| 4,086,222 A | 4/1978 | Lindquist et al. |
| 4,197,238 A | 4/1980 | Murata et al. |
| 5,229,498 A | 7/1993 | Eketorp |
| 5,250,662 A | 10/1993 | Chang |
| 5,250,663 A | 10/1993 | Tenold |
| 5,846,930 A | 12/1998 | Ristol Debart et al. |
| RE36,259 E | 7/1999 | Tenold |

OTHER PUBLICATIONS

Cohen et al., Preparation and Properties of Serum and Plasma Proteins. IV. A System for the Separation into Fractions of the Protein and Lipoprotein Components of Biological Tissues and Fluidds, J. American Chem. Soc., 1946, vol. 68, pp. 459–475.

Loeliger, E.A. et al., "Aluminum Contamination of Albumin—Replacement Solutions," University Hospital—Letter to the Editor, vol. 312, No. 21.

Milliner, Dawn S., M.D., et al., Inadvertent Aluminum Administration During Plasma Exchange Due to Aluminum Contamination of Aluminum—Replacement Solutions, The New England Journal of Medcine, 01/85, vol. 312, No. 3, pp. 165–168.

Quagliaro, D.A., et al., "Aluminum in Albumin for Injection," Journal of Parental Science and Technology, Nov.–Dec. 1988, vol. 42, No. 6, pp. 187–190.

Rainbow, E. Barrett et al., Aluminum in Parenteral Products: "Analysis, Reduction, and Implications for Pediatric TPN," Journal of Parenteral Science & Technology, May–Jun. 1989, vol. 43, No. 3, pp. 132–139.

*Primary Examiner*—Brenda Brumback
*Assistant Examiner*—B. Dell Chism
(74) *Attorney, Agent, or Firm*—Christie, Parker & Hale, LLP

(57) ABSTRACT

A method is provided for removing citrate, aluminum, and other multivalent ions and contaminants from proteins by adjusting the pH of a solution containing the protein to a pH from about 7 to about 10, and diafiltering the pH-adjusted solution against aqueous solutions which have a low level of ions.

33 Claims, 12 Drawing Sheets

Figure 1: DIAFILTRATION OF PROTEIN SOLUTION AGAINST DEIONIZED WATER

Reduction of Citrate and Aluminum in Albumin
(Example 6, Lot One: DS Samples)

Reduction of Citrate and Aluminum in Albumin
(Example 6, Lot Two: DS Samples)

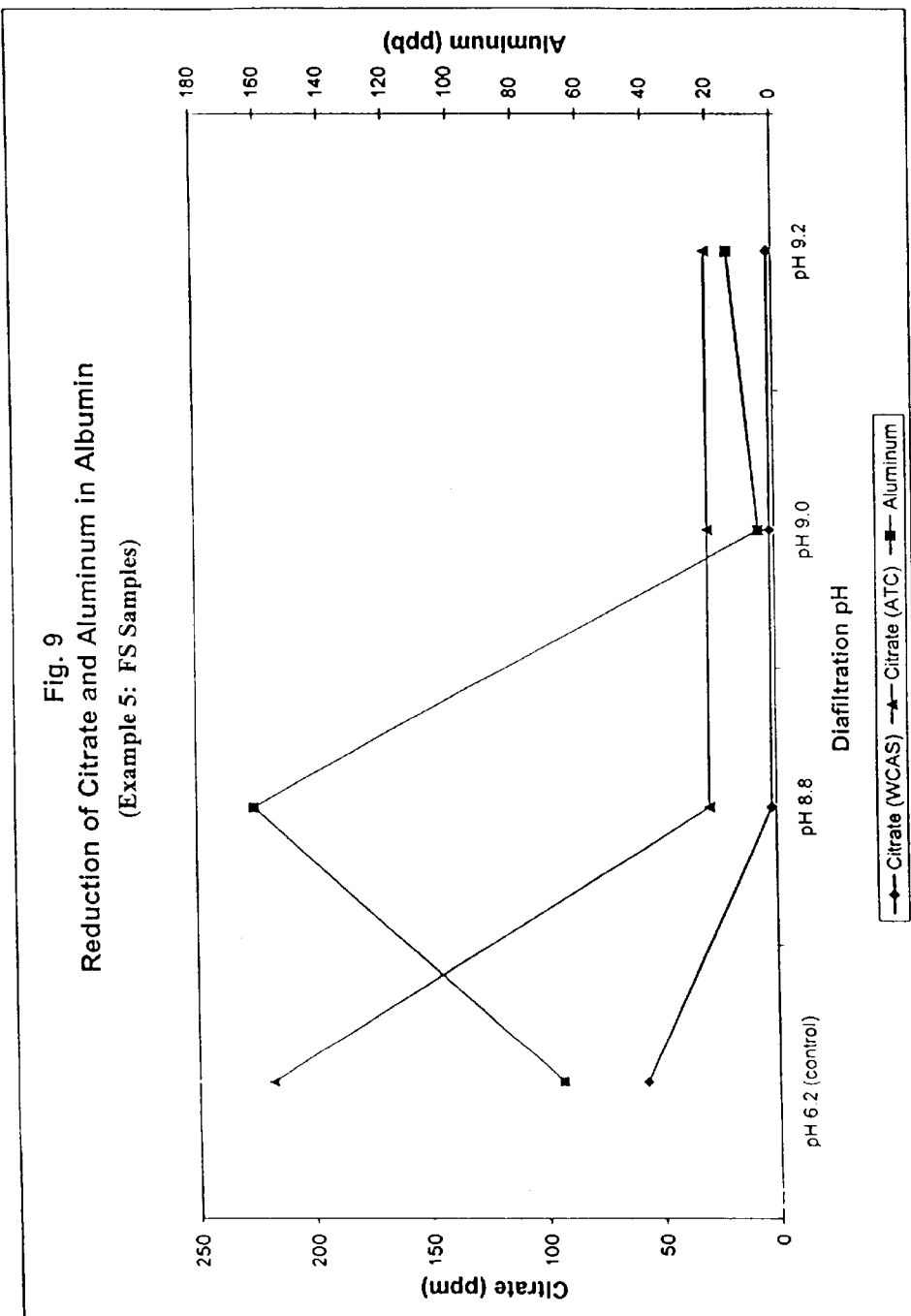

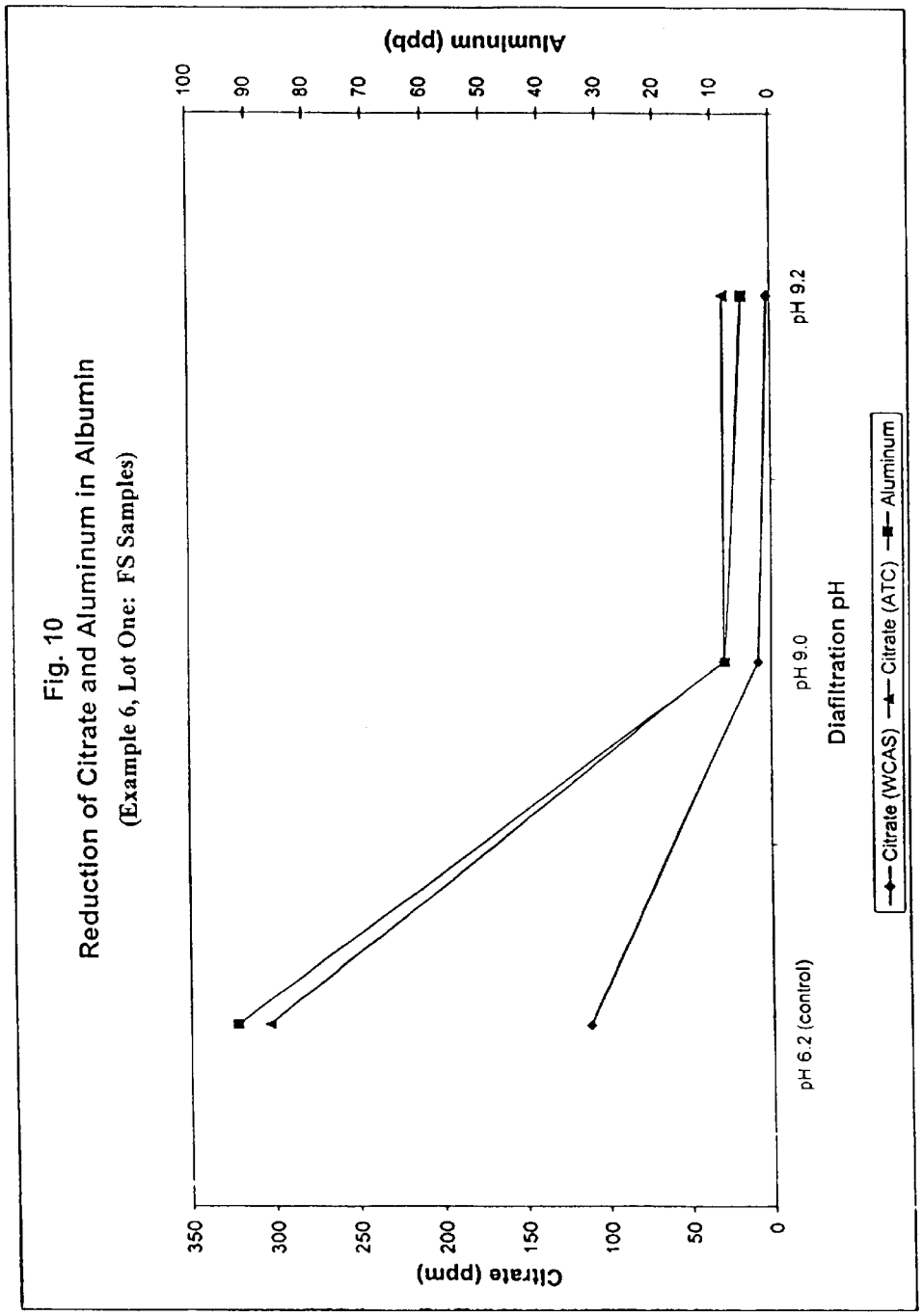

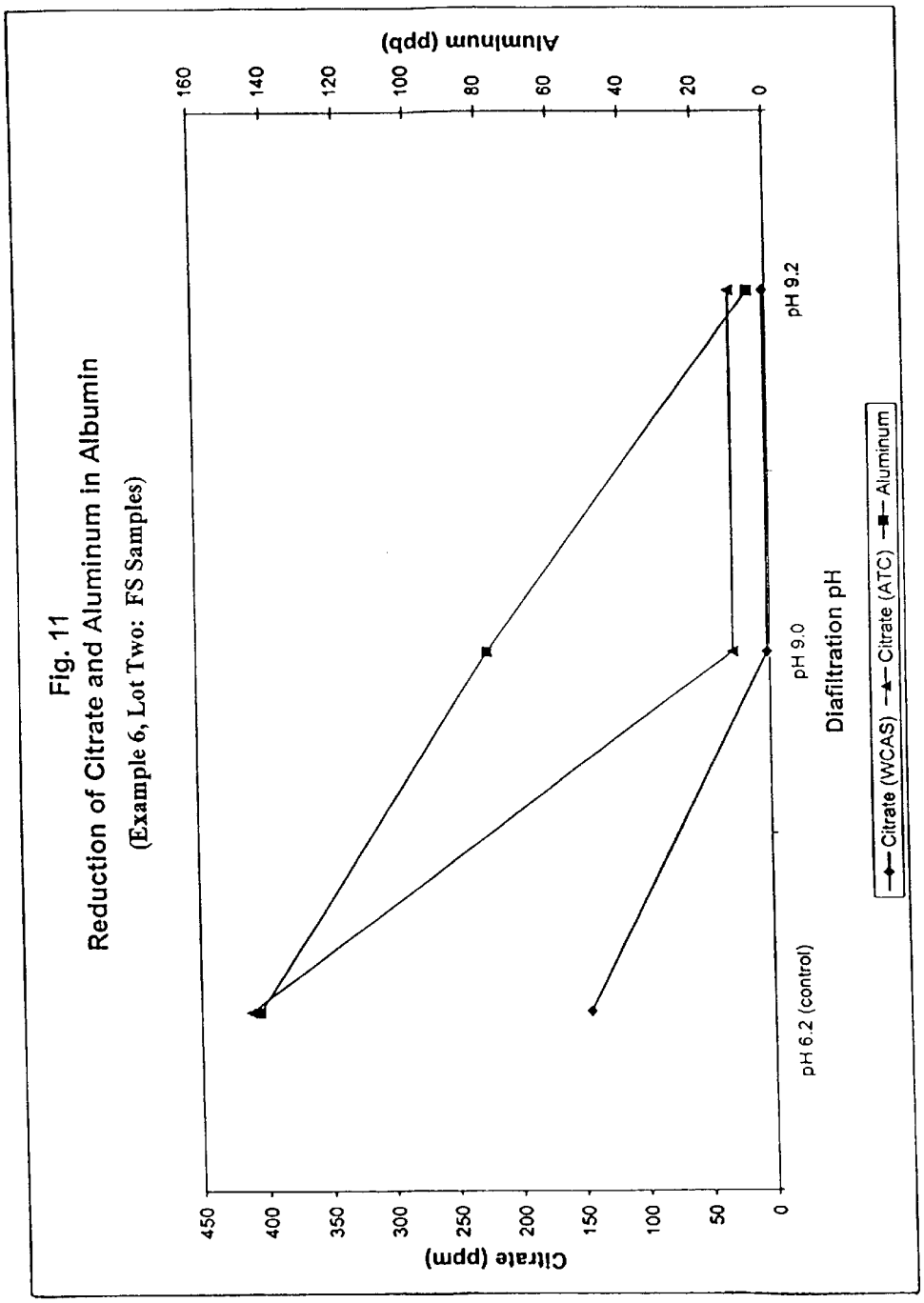

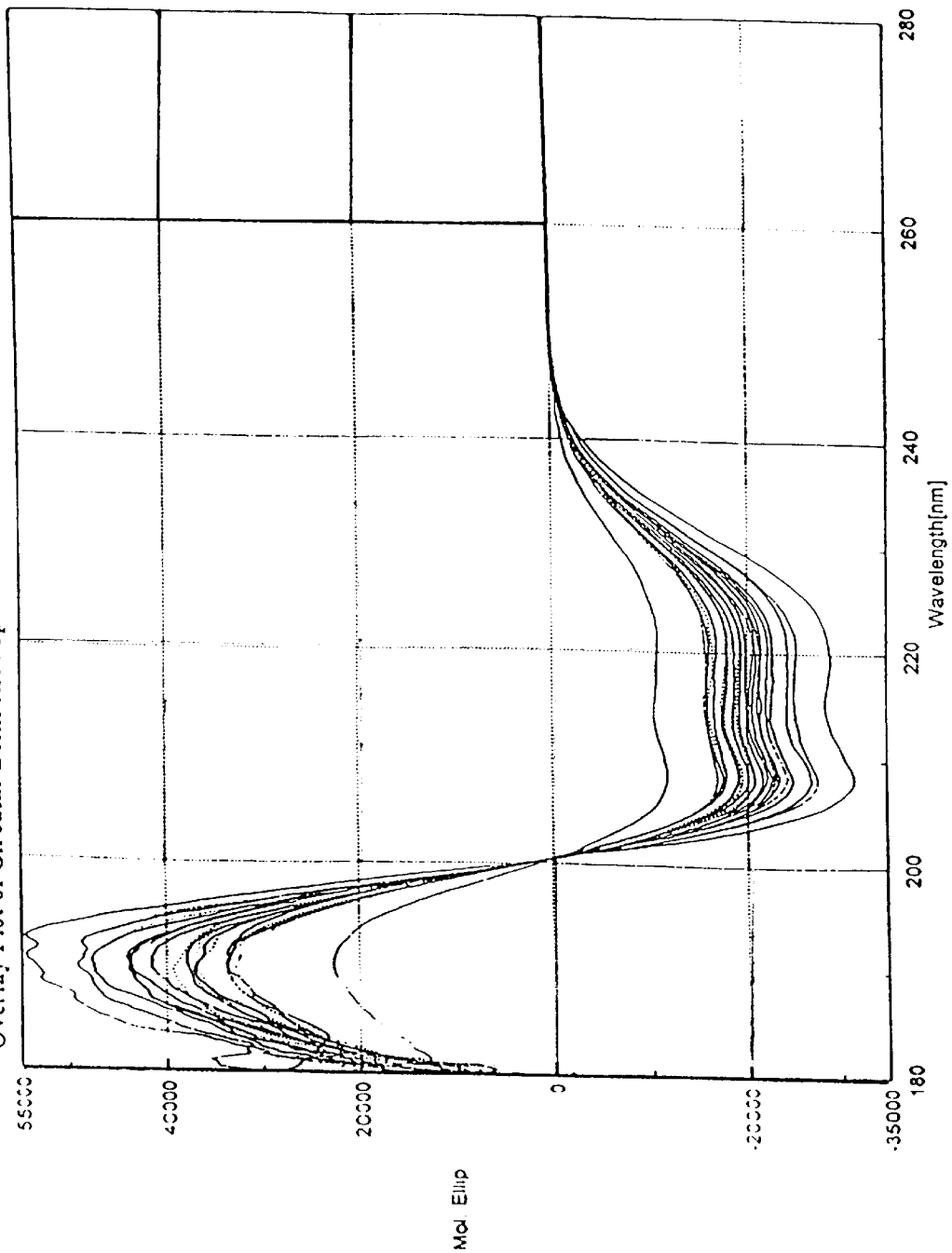

METHOD TO REMOVE CITRATE AND ALUMINUM FROM PROTEINS

CROSS-REFERENCE TO RELATED APPLICATIONS

This is a continuation-in-part of abandoned application Ser. No. 09/752,138, filed on Dec. 26, 2000, the entire contents of which is hereby expressly incorporated by reference.

FIELD OF INVENTION

This invention relates to a method useful for removing citrate, aluminum and other multivalent ions from biologically active proteins. The method is particularly useful for removing aluminum and citrate ions from solutions containing albumin.

BACKGROUND OF THE INVENTION

Biologically active proteins are frequently administered to humans as therapeutic agents. It is important that such proteins be free from contaminants that may cause adverse effects. It is known, for example, that purified human serum albumin (albumin) used widely in solutions intended for intravenous administration and as a plasma volume expander, may contain levels of aluminum that are unacceptable for use in humans.

The presence of aluminum in humans has been linked to senile dementia of the Alzheimer type and to neurofibrillary degeneration. Aluminum administered intravenously can accumulate in tissues and organs, such as the brain, and poses a particular threat to patients with impaired renal function who are unable to adequately eliminate the aluminum from the body. In such patients, aluminum contamination of dialysis solutions has been linked to osteomalacia, microcytic anemia and dialysis encephalopathy. As a consequence, albumin sold in Europe for intravenous administration is required to have a level of aluminum less than or equal to 200 ppb in solutions having 5, 20 or 25% protein concentration, a level that should be maintained throughout the dating period of the albumin product. The adverse effects of other metals, such as iron, lead, mercury, chromium, copper and nickel, have also been documented.

It has been shown that albumin acquires aluminum from a number of sources, including the diatomaceous earth used during albumin processing, glass containers, clay-filled elastomeric enclosures, and depth filters containing diatomaceous earth. (Quagliaro, D. A. et al., Aluminum in Albumin for Injection, Journal of Parenteral Science & Technology, 42(6), 187–190 (1988)).

Some solutions show an increase in the level of aluminum during storage, attributed to the extraction of aluminum from glass containers. Glass containers appear to be a significant source of aluminum contamination, as many such containers are composed of 1 to 5% aluminum. Factors that contribute to the level of aluminum in a protein solution are the storage conditions of the solution in glass containers and the nature of solutes present in the protein solution. For example, carboxylic acids which have an alpha hydroxy group, such as citrate anions, are good chelators of metal ions and are well known for their solubilizing effect on aluminum-containing substances.

Citrate ions are introduced into plasma-derived proteins during the normal plasmapheresis procedure, which involves the collection of plasma in the anticoagulant sodium citrate. For example, solubilized Cohn Fraction V powder, the starting material in the preparation of albumin solutions by the acetone process, has a citrate content of about 7.6 mM to about 9.7 mM (about 2235 ppm to about 2853 ppm). Thus, in addition to ensuring a low level of aluminum in albumin and other protein solutions to be administered to humans, it is also important to ensure a low level of citrate to avoid possible leaching of aluminum from glass containers by citrate ions during storage.

Multivalent aluminum ions, as with other multivalent ions, bind to proteins, and attempts to remove these ions with chelating agents such as EDTA have been largely unsuccessful. Ultrafiltration dialysis techniques have been used to remove multivalent ions from proteins such as albumin. These protocols rely on the displacement of the multivalent ions bound to the protein by monovalent ions during dialysis. For example, U.S. Pat. No. Re. 36,259 describes the use of a 3% aqueous salt solution, such as sodium chloride or sodium acetate, in a diafiltration system to displace aluminum ions from albumin. Similarly, U.S. Pat. No. 5,229,498 describes the displacement and removal of multivalent ions from proteins by diafiltration against an aqueous solution containing monovalent alkali metal ions or ammonium ions in a concentration from about 0.15 M up to saturation.

In the above cases, however, the diafiltered protein contains bound monovalent ions. As a consequence, it is necessary to subject the protein to an additional round of diafiltration, usually against deionized water, to remove the monovalent ions. A method in which both citrate ions and aluminum ions, as well as other multivalent ions, are removed from proteins without the necessity for a second procedure to remove the monovalent ions would thus be preferred.

SUMMARY OF THE INVENTION

The present invention is directed to a process for removing citrate, aluminum, and other multivalent ions and contaminants from proteins by adjusting the pH of a solution containing the protein to a pH from about 7 to about 10, and diafiltering the pH-adjusted solution against pure water.

BRIEF DESCRIPTION OF THE DRAWINGS

These and other features, aspects, and advantages of the present invention will be more fully understood when considered with respect to the following detailed description, appended claims, and accompanying drawings, wherein:

FIG. 9 is a graph illustrating the effect of diafiltration pH on the reduction of citrate and aluminum ions in a 20% albumin solution (final container samples), prepared as in Example 5.

FIG. 10 is a graph illustrating the effect of diafiltration pH on the reduction of citrate and aluminum ions in a 25% albumin solution (final container samples), Lot One, prepared as in Example 6.

FIG. 11 is a graph illustrating the effect of diafiltration pH on the reduction of citrate and aluminum ions in a 25% albumin solution (final container samples), Lot Two, prepared as in Example 6.

FIG. 12 is an overlay plot of the circular dichroism (CD) spectra for samples taken during the preparation of solutions of 20% and 25% albumin.

DETAILED DESCRIPTION

Figure 1:
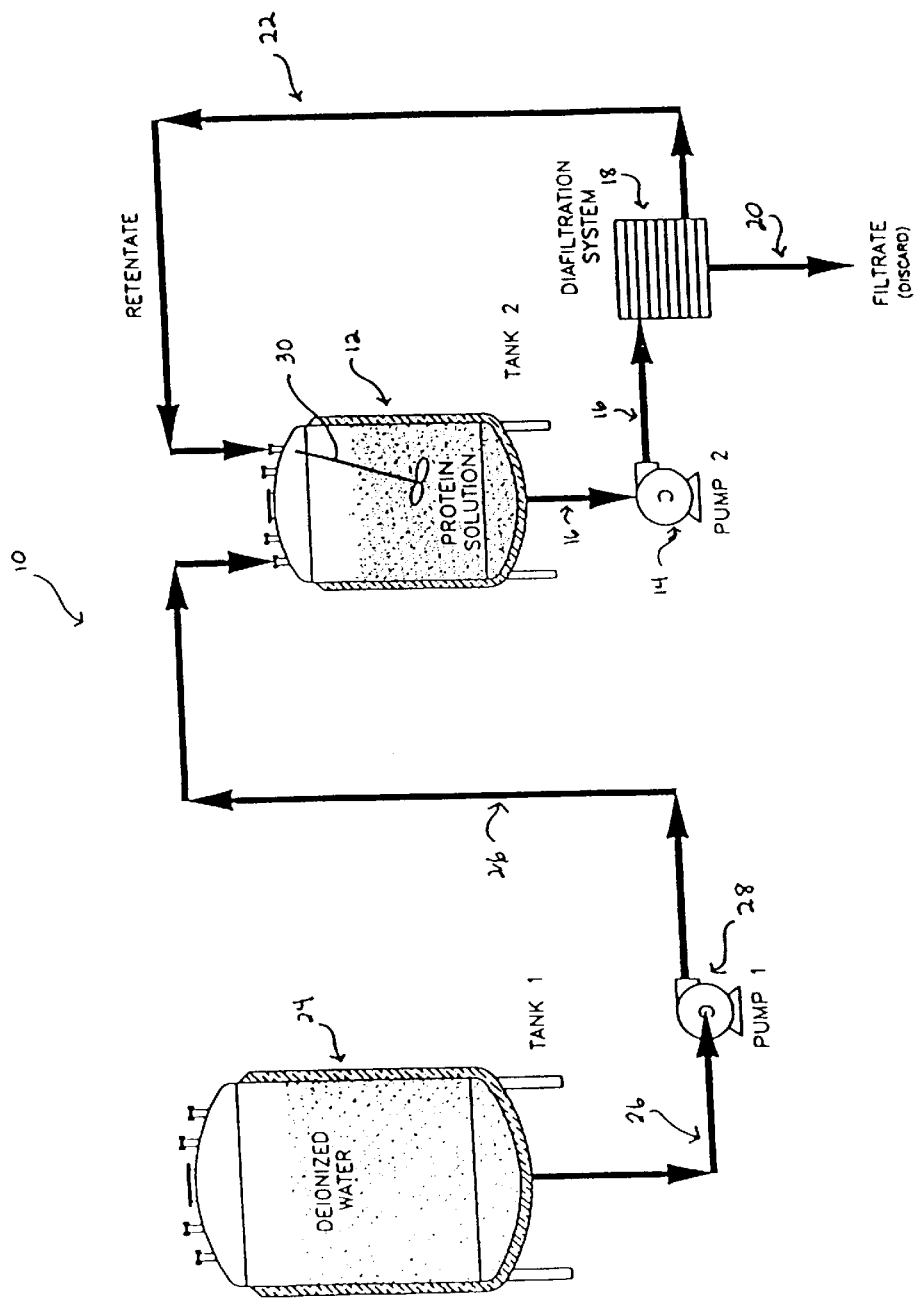
FIG. 1 is a schematic drawing of a system for the diafiltration of protein solution against pure water according to practice of the present invention.

The process of this invention provides for a simple, cost effective and efficient procedure for removing citrate, aluminum, and other multivalent ions and contaminants from proteins. The process of this invention is particularly useful for removing citrate and aluminum ions from albumin.

Starting material for the process may be any aqueous protein-containing solution which also contains citrate and/or aluminum ions. For example, the starting material may be commercially prepared albumin, solubilized Fraction V powder or Fraction V paste from the Cohn method, described in Cohn et al., *J. Amer. Chem. Soc.*, 68: 459–475 (1946), hereby incorporated by reference in its entirety, other blood-plasma-derived fraction, or any other aqueous solution containing albumin or other plasma proteins. U.S. Pat. No. 5,250,662, hereby incorporated by reference in its entirety, describes a method for purifying albumin suitable as a starting material.

Other examples of starting materials suitable for practice of this invention include, but are not limited to, aqueous solutions containing immunoglobulins, Factor VIII, Factor IX, alpha-1-proteinase inhibitor and/or prothrombin complex.

The initial protein-containing solution is first adjusted to a pH value from about 7 to about 10, with a base such as 1 N NaOH. In one embodiment, solutions containing albumin are adjusted to a pH from about 8.8 to about 9.2. The protein solution preferably is pre-filtered to remove precipitated protein or other particulate matter.

The protein-containing solution is then applied to a diafiltration system. The diafiltration system is selected to contain a diafilter membrane with a pore size smaller than the molecular weight of the protein, so as to allow multivalent ions such as aluminum ions and citrate ions, as well as salts, solvents, and other small molecules, to pass through the diafilter membrane while retaining the protein. Diafilter membranes suitable for use in removing citrate and aluminum from albumin solutions, for example, include Millipore UF-10 KD filter membranes and Millipore UF-30 KD filter membranes (Millipore Corporation, Bedford, Mass.).

The protein-containing solution is passed through the diafiltration system in a direction parallel to the diafilter membrane or membranes. A pressure gradient is applied over the filter. As the protein-containing solution moves across the diafiltration membrane(s), contaminants pass through the diafiltration membrane(s) as filtrate while the protein is retained as retentate. Pure water is added to the retentate and the resulting diluted retentate is recycled for further diafiltration. This process is repeated until the desired reduction of contaminants has been achieved.

As used herein, "pure water" means any aqueous solution having a low concentration of ions, including deionized water and distilled water. Pure water also includes Water for Injection, Bacteriostatic Water for Injection, Sterile Water for Inhalation, Sterile Water for Injection, Water for Irrigation, and Purified Water, as described in the 1995 United States Pharmacopoeia, National Formulary 18 (hereby incorporated by reference in its entirety).

Turning to FIG. 1, there is shown a system 10 useful in the practice of the present invention. The pH-adjusted protein solution is placed into a source tank 12. A pump 14 causes the solution to flow through a hose 16 into a diafiltration device 18 containing a diafilter membrane (not shown). The filtrate is removed from the diafiltration device through a pipe 20, and the retentate is recirculated back to the source tank through a pipe 22.

Pure water, for example, deionized water, contained in a water tank 24, is pumped into the source tank through a hose 26 by a pump 28. A stirring device 30 mixes the pure water with the retentate in the source tank.

In one preferred embodiment, the pure water is added continuously to the source tank 12 at a rate equal to the rate at which filtrate is removed from the diafiltration device. In this embodiment, the volume of the protein solution/retentate is kept constant ("constant volume wash diafiltration"). The retentate is continuously recirculated through the diafiltration device and the source tank until the amount of pure water added to the retentate is equal to at least about 3-times the volume or weight of the initial protein solution, or until the desired reduction of contaminants is achieved.

In a second preferred embodiment, the pure water is added to the retentate in batches, rather than continuously. In this "batch-wise diafiltration" embodiment, the volume of the retentate decreases as filtrate is removed and the concentration of the protein in the retentate increases. When the protein concentration in the retentate has increased between 2-fold and 10-fold, an amount of pure water sufficient to restore the volume of the retentate to the initial volume of the protein solution is added to the source tank. The process of recirculating the retentate through the diafiltration device and the source tank and the batch-wise addition of pure water to the source tank continues until the desired concentration of multivalent ions is achieved.

Examples of the method of the present invention are set forth below.

EXAMPLE 1

Constant Volume Wash Diafiltration of Albumin Against Deionized Water

About 40 mL of a commercially produced 25% albumin solution at pH 7.2 was diafiltered according to practice of the present invention. As the albumin solution was circulated through a diafiltration device containing a 10 KD Millipore® UF membrane filter, the filtrate was removed and deionized water was continuously added to the retentate at a rate equal to the rate at which the filtrate was removed. Diafiltration was repeated until a volume of about 280 mL deionized water had been added. The diafiltered albumin solution was then tested for aluminum and citrate.

Samples were tested for citrate ions at West Coast Analytical Services (WCAS; Santa Fe Springs, Calif.). In the ion chromatography method used by WCAS, citrate ions were detected by suppressed conductivity and were quantified by reference to an external standard.

The aluminum tests were also conducted at WCAS, using Inductively Coupled Plasma Mass Spectroscopy (ICPMS) techniques. In this method, positive ions generated by plasma are introduced into a vacuum interface. Following the interface is a quadrapole mass spectrometer, which acquires data for a range of elemental isotope masses following sample introduction. The data is recorded and collected in a multichannel analyzer, and is used to calculate the concentration of aluminum by comparison with standards.

The results are shown in Table 1.

TABLE 1

Citrate and Aluminum Levels in 25% Albumin Before and After Diafiltration

| Sample | Citrate Level (ppm) | Aluminum Level (ppb) |
| --- | --- | --- |
| Starting Material (25% Albumin) | 1236 | 258 |
| Diafiltered solution, pH 7.2 | 35 | 48 |
| Reduction after diafiltration (%) | 97% | 81% |

As shown in Table 1, 97% of the citrate in the commercially prepared 25% albumin solution, pH 7.2, was removed during diafiltration against deionized water, while 81% of the aluminum was removed.

EXAMPLE 2

Effect of pH on the Removal of Aluminum and Citrate During Constant Volume Wash Diafiltration of Albumin A solution of commercially produced 25% albumin was diluted 3-fold with deionized water. The diluted albumin solution was divided into three samples. Using 1 N NaOH, the pH of the first sample was adjusted to 8.1, the pH of the second sample was adjusted to 9.1, and the pH of the third sample was adjusted to 9.9.

About 50 mL from each sample was separately subjected to constant volume wash diafiltration against deionized water, using a 10 KD Millipore UF membrane filter. Diafiltration was continued until about 350 mL of deionized water had been added. The citrate and aluminum levels in the diluted albumin solution before and after diafiltration were measured as discussed above. The results are shown in Table 2.

TABLE 2

Citrate and Aluminum Levels in Albumin Solution Before and After Diafiltration

| Sample | Citrate Level (ppm) | Aluminum Level (ppb) |
| --- | --- | --- |
| Starting Material (3-fold diluted 25% Albumin) | 280 | 74 |
| Diafiltered solution, pH 8.1 | <50 | 10 |
| Diafiltered solution, pH 9.1 | <50 | <10 |
| Diafiltered solution, pH 9.9 | <50 | <10 |

As shown in Table 2, the citrate levels in commercial albumin were reduced to below 50 ppm at all pH conditions tested. The aluminum level at pH 8.1 was reduced from 74 ppb to 10 ppb, while the aluminum level at pH 9.1 and 9.9 was reduced to below 10 ppb.

EXAMPLE 3

Cohn Fraction V Paste—Effect of pH on Albumin and Citrate Ion Levels Following Constant Volume Wash Diafiltration Against Deionized Water An albumin solution containing approximately 7% protein was prepared by suspending Cohn Fraction V paste in deionized water. After adjusting the pH to 4.6, the albumin solution was treated with previously equilibrated DEAE Sephadex A-50 resin. A portion of the pre-filtered pass-through albumin solution was taken and five 50-mL aliquots were prepared from this solution. The first aliquot was adjusted to pH 5.0, the second to pH 7.0, the third to pH 8.0, the fourth to pH 9.0, and the fifth to pH 10.0.

Each aliquot was individually subjected to constant volume wash diafiltration against deionized water, using a 10 KD Millipore® UF membrane filter. Diafiltration continued until about 350 mL deionized water had been added. The citrate and aluminum levels in the albumin solution were measured before and after diafiltration. The results are shown in Table 3.

TABLE 3

Citrate and Aluminum Levels in Albumin Solution Before and After Diafiltration

| Sample | Citrate Level (ppm) | Aluminum Level (ppb) |
| --- | --- | --- |
| Starting Material (In-process albumin solution at approximately 7% protein) | Not Available | 84 |
| Diafiltered solution, pH 5.0 | 433 | 82 |
| Diafiltered solution, pH 7.0 | 180 | 66 |
| Diafiltered solution, pH 8.0 | 97 | 36 |
| Diafiltered solution, pH 9.0 | 64 | 35 |
| Diafiltered solution, pH 10.0 | 20 | 50 |

The results shown in Table 3 indicate a decreasing trend of citrate and aluminum levels with diafiltration of the albumin solutions under increasing pH conditions. In general, both the levels of aluminum and citrate declined with increasing pH, although the level of aluminum at pH 10 was slightly elevated over the level at pH 9.0 and pH 8.0.

EXAMPLE 4

Cohn Fraction V Powder—Effect of Diafiltration at pH 10 Against Deionized Water on Aluminum and Citrate Levels Albumin solution containing approximately 7% protein was prepared from Cohn Fraction V powder, which was obtained from acetone-treated Cohn Fraction V paste. The pH of the albumin solution was adjusted to about 10.

The pH adjusted albumin solution was diafiltered against deionized water using a diafiltration device containing a 30 KD Millipore® UF membrane filter. The albumin solution from the source tank was pumped into the diafiltration device. The retentate was recirculated back to the source tank while the filtrate was removed. Deionized water was added to the source tank continuously at about the same rate as the filtrate was removed. When an amount of deionized water equal to about 7 times the original weight of the protein solution had been added, the diafiltration process was stopped. Samples of protein solution were collected and tested for citrate and aluminum. The test results are shown in Table 4.

TABLE 4

Citrate and Aluminum Levels in Albumin Solution Before and After Diafiltration

| Sample | Citrate Level (ppm) | Aluminum Level (ppb) |
| --- | --- | --- |
| Starting material (In-process albumin solution at approximately 7% protein) | 1700 | 49 |
| Diafiltered solution, pH 9.9 | <2 | 2 |

As shown in Table 4, after adjusting the pH of the protein solution to about 10 and diafiltering the solution against deionized water, the citrate level was reduced to less than 2 ppm from the initial value of 1700 ppm and the aluminum level was reduced from 49 ppb to 2 ppb.

EXAMPLE 5

Preparation of 20% Albumin from Solubilized Cohn Fraction V Powder Adjusted to pH 6.2, 8.8, 9.0, or 9.2

About 1.5 Kg of Fraction V powder, obtained from acetone-treated Cohn Fraction V paste, was suspended in cold deionized water at 0 to 10° C. to yield a solution containing approximately 8% protein. The pH was adjusted to about 6.5±0.5 with the temperature maintained at 0 to 10° C. The pH adjusted albumin solution was clarified by filtration through a CUNO CPX90SP depth filter with filter aid.

The clarified solution was divided into four sub-lots of 4 Kg each, and the pH of each sub-lot was adjusted to 6.2 (control), 8.8, 9.0, or 9.2 with 1 N NaOH. Each pH adjusted sub-lot was diafiltered twice with a total volume of cold (from about 2° C. to about 8° C.) deionized water equal to 5 times the weight of the starting solubilized Fraction V solution ("5× volume"). The protein concentration at the completion of diafiltration was 13±3%. The pH of the diafiltered albumin solution was adjusted to pH 6.70–6.85 with 0.5 N HCl (for the pH 6.2 control) or 1.0 N HCl (for the pH 8.8, 9.0 and 9.2 sub-lots).

The diafiltered albumin solution was stabilized with sodium caprylate and sodium acetyl tryptophan to a final concentration of 0.08 millimole each per gram of protein. After clarification by filtration, the solution was heated for two hours at 60±0.5° C. The heated albumin solution was rapidly cooled to a temperature of 5 to 10° C., clarified by filtration, and concentrated to a protein solution of 23 to 26%.

The solution was re-stabilized with sodium caprylate and sodium acetyl tryptophan to a level of 0.08 millimole each per gram of albumin. The pH was adjusted to 6.9±0.5, the sodium adjusted to 145±15 mEq per liter and the protein adjusted to about 20%.

The solution was sterile filtered through sterilized bacteria retentive filters and filled into sterilized bottles (type II glass) and stoppered with chlorinated rubber stoppers. The sealed bottles were heat treated for not less than 10 hours or more than 11 hours at 60±0.5° C.

EXAMPLE 6

Preparation of 25% Albumin from Solubilized Cohn Fraction V Powder Adjusted to pH 6.2, 9.0, or 9.2

Two separate lots (Lot One and Lot Two) of 25% albumin were prepared from solubilized Cohn Fraction V Powder as described in Example 5, except that the clarified solution for each lot was divided into 3 sub-lots of 4 Kg each, with the pH of each sub-lot adjusted to 6.2 (control), 9.0 or 9.2, and the final heated albumin solutions from each sub-lot were concentrated to a protein solution of about 25%.

Figure 2:
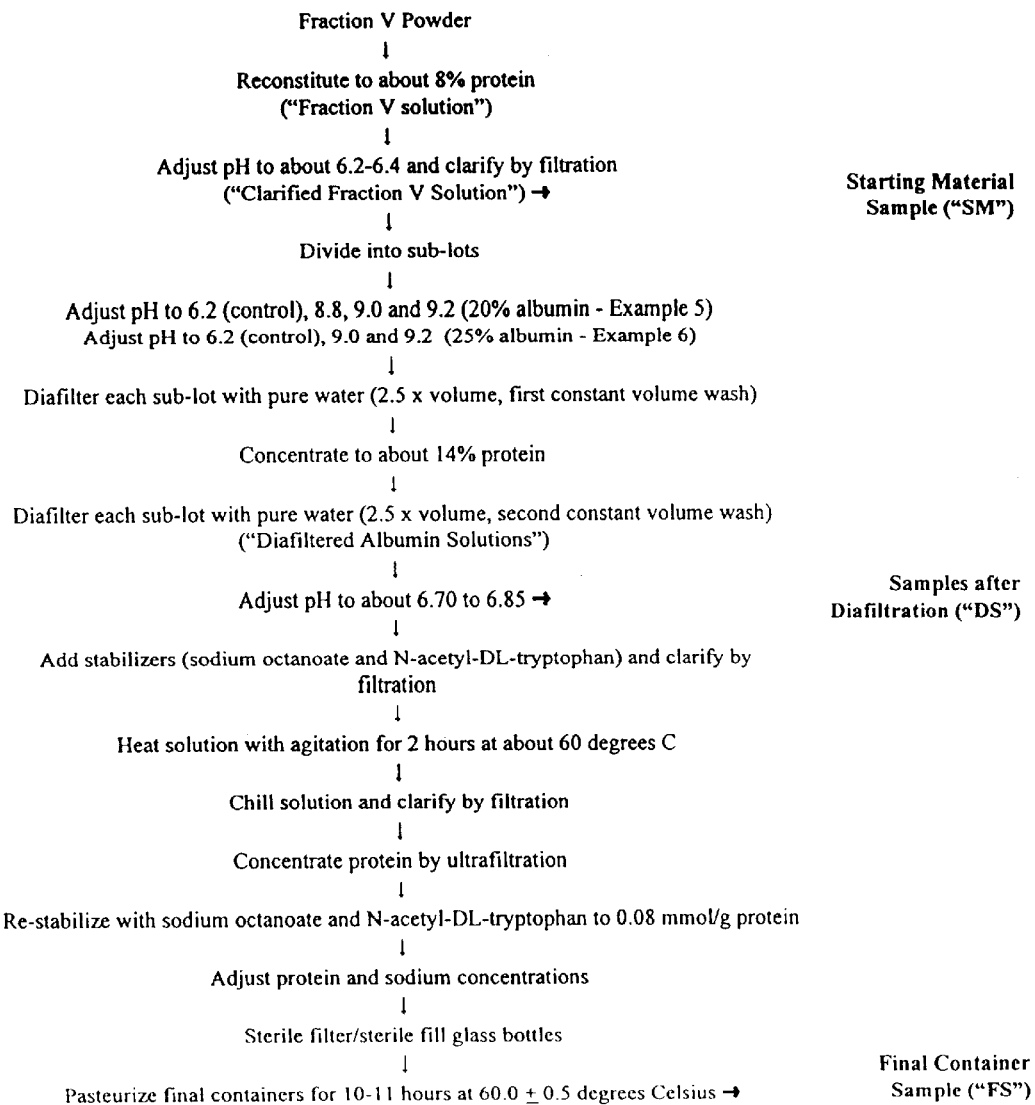
FIG. 2 is a flowchart illustrating the preparation of diafiltered albumin solution from Cohn Fraction V powder according to the practice of the present invention, and indicating the sampling points for testing citrate and aluminum levels of the albumin solution when diafiltered against pure water at pH 6.2, 8.8, 9.0, or 9.2.

Samples for testing were taken at three stages in the process of preparing the 20% and 25% Albumin (Examples 5 and 6): before diafiltration (Starting Material or "SM"), after diafiltration (post pH adjustment to 6.70–6.85; Diafiltered Sample or "DS"), and after pasteurization in the final sterile glass containers (Final Container Sample or "FS"). A summary of the process for preparing albumin, with the three sampling points indicated, is shown in FIG. 2.

EXAMPLE 7

Diafiltration of Fraction V Solution at Different pH and Different Diafiltration Wash Volumes The effect of increasing the pH of the clarified Fraction V solution during diafiltration (to pH 8.8, 9.0, or 9.2) on the reduction of citrate was determined. Diafiltration was also performed at pH 6.2 to serve as a control. Samples of diafiltered Fraction V solution ("DS") from Example 5 were tested for citrate both at West Coast Analytical Services (WCAS; Santa Fe Springs, Calif.) and at Alpha Therapeutic Corporation (ATC; Los Angeles, Calif.).

The ion chromatography method used by WCAS to measure citrate levels, as described above, has a lower detection limit of 2 ppm. In the calorimetric method used at ATC, standard citrate solutions and deproteinized samples were mixed and reacted with pyridine and acetic anhydride. After a period of about 45 minutes, the optical densities at 425 nm ($OD_{425}$) of these solutions were measured. The citrate ion content of each sample was then calculated and determined from a standard curve. This method has a lower detection limit of 0.1 mM (29 ppm). All citrate values below the detection limit were taken as detection limit values in FIGS. 3–5, discussed below.

Figure 3:
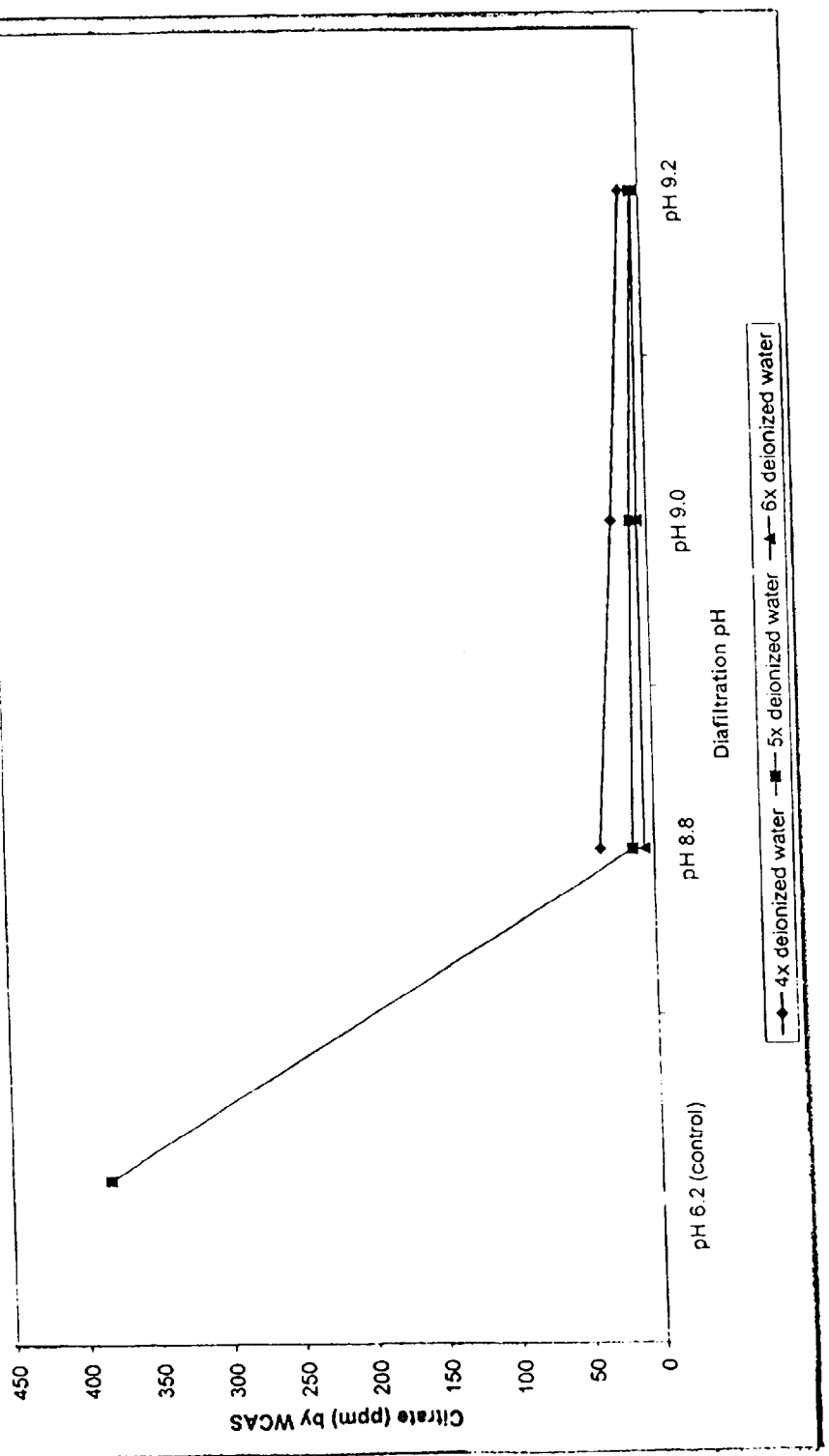
FIG. 3 is a graph illustrating the effect of pH (6.2, 8.8, 9.0, or 9.2) on the reduction of citrate in clarified Fraction V solutions diafiltered against different volumes of deionized water.

Additional samples were taken from diafiltered Fraction V solutions prepared as in Example 5 except that the diafiltration constant volume wash was either 4× volume or 6× volume. As shown in FIG. 3, diafiltration at pH 8.8, 9.0 and 9.2 against cold (about 2° C. to about 8° C.) deionized water yielded solutions with lower amounts of citrate (between about 38 and 5 ppm) compared to diafiltration at pH 6.2 (383 ppm).

Figure 4:
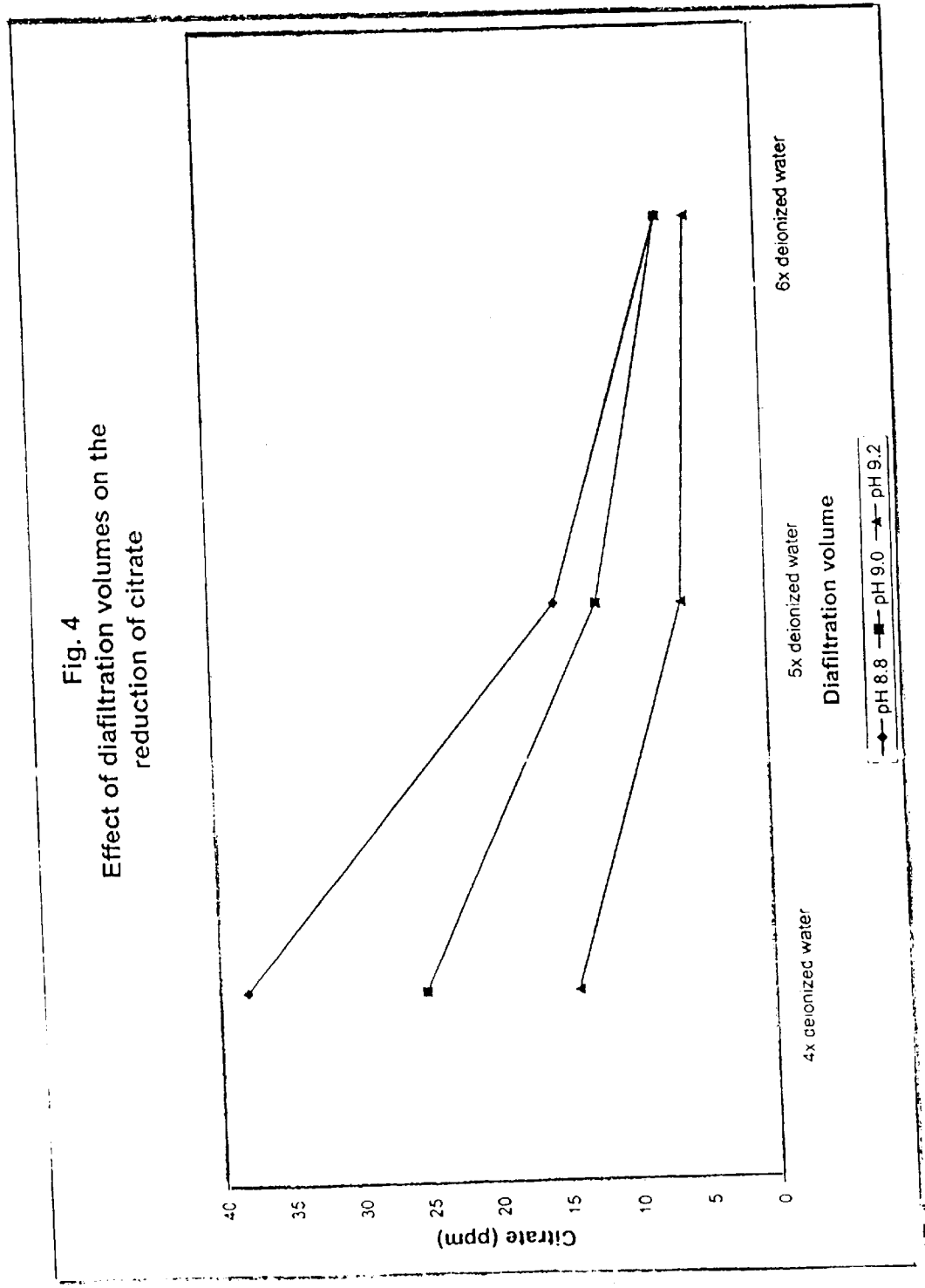
FIG. 4 is a graph illustrating the effect of diafiltration volume on the reduction of citrate in clarified Fraction V solutions at pH 8.8, 9.0 or 9.2.

Low levels of citrate (less than 50 ppm) were also seen in samples in which the wash volume was either 4× volume or 6× volume, when diafiltered at pH 8.8, 9.0 or 9.2. See FIGS. 3 and 4. As shown in FIG. 4, at each pH used, the higher the volume of deionized water used to diafilter the clarified Fraction V solution, the greater the reduction in citrate.

Figure 5:
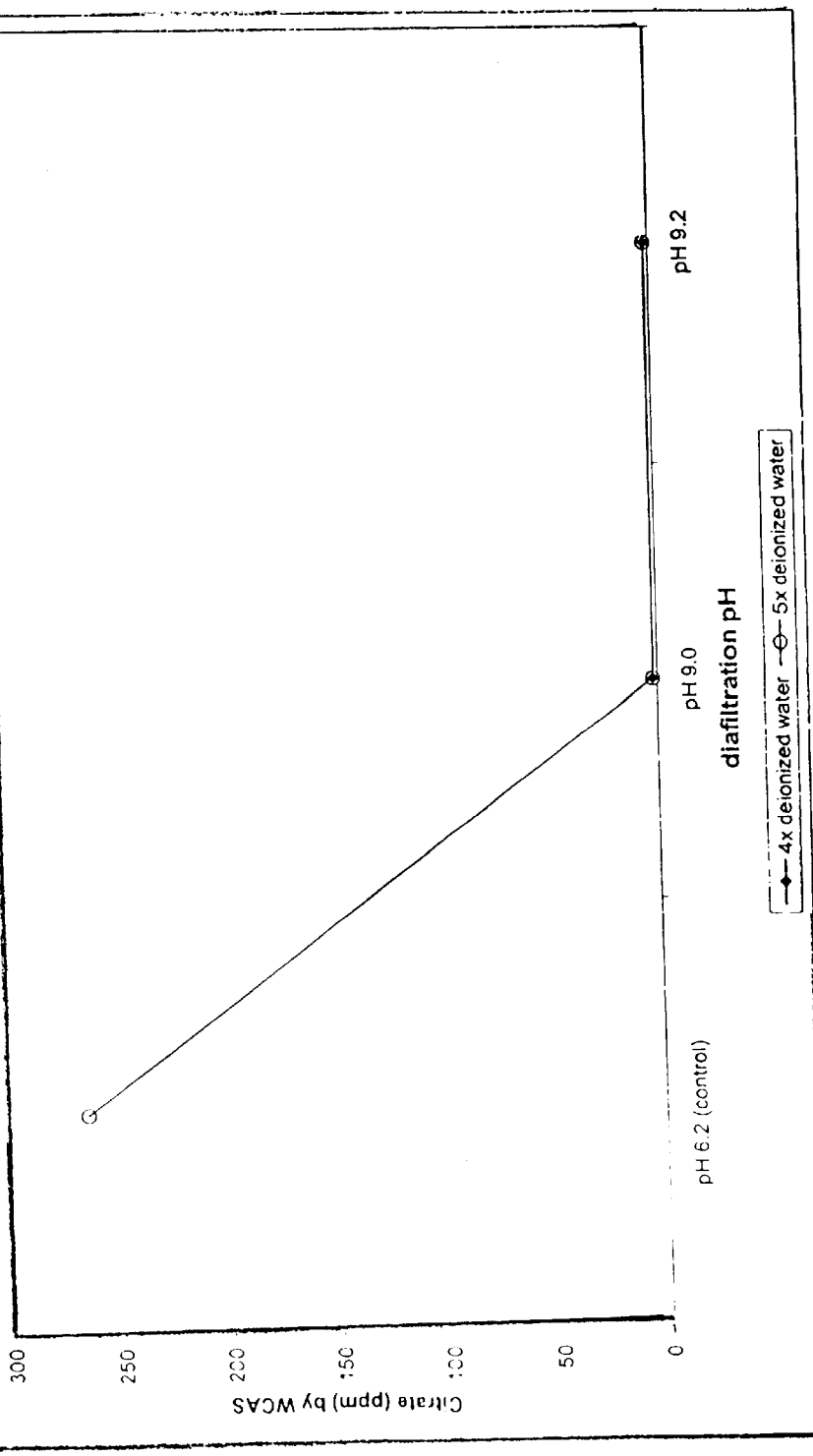
FIG. 5 is a graph illustrating the effect of pH (6.2, 9.0, or 9.2) on the reduction of citrate in clarified Fraction V solutions diafiltered against different volumes of deionized water.

The same results were found when a lot of 25% albumin was prepared as in Example 6, diafiltering the clarified Fraction V solution at pH 6.2 (control), pH 9.0 and 9.2 against either 4× volume or 5× volume deionized water. As shown in FIG. 5, at both pH 9.0 and 9.2, the amount of citrate following diafiltration at either wash volume was below the detection limit of 2 ppm, compared to 264 ppm obtained for the control (pH 6.2, 5× volume).

EXAMPLE 8

Citrate and Aluminum Levels Before and After Diafiltration of Clarified Fraction V and in Final Container Solutions of 20% and 25% Albumin Citrate and aluminum levels were measured for each of three samples (SM, DS and FS) from the preparation of 20% albumin in Example 5 and from the preparation of Lots One and Two of the 25% albumin in Example 6. The results are shown in Tables 5, 6 and 7 and FIGS. 6 through 11.

Aluminum tests were conducted at ATC using graphite furnace atomic absorption (GFAAS), which involves the generation of atoms by means of an electrically heated graphite furnace atomizer. After drying and ashing to remove solvent, organic molecules and/or inorganic material, the sample is atomized to generate free atoms in a confined zone. An absorption signal produced by GFAAS is a sharp peak, the area of which can be related to the amount of the analyte element present in the sample. A Varian SpectrAA-400 Zeeman Atomic Absorption Spectrometer equipped with a Varian graphite furnace model GTA96Z and a Varian autosampler PSD96 with programmable sampling was used for the aluminum determinations. Samples diluted to 2.5% protein were introduced into a pyrolytic graphite platform inside a pyrolytically coated plateau tube. The atomic absorption measurement was performed at 309.3 nm.

Because the protein concentrations in the samples collected from the three sampling points (SM, DS and FS) are different, the aluminum values reported in Table 5 and FIGS. 6 through 11 were normalized to 2.5% protein to maintain consistency.

Citrate tests were conducted at both ATC and WCAS, as described above. All citrate and aluminum results that were below the detection limit, as shown in Tables 5, 6 and 7, were assigned their respective detection limit value to draw graphs shown in FIGS. 6 through 11.

TABLE 5

Aluminum Test Results

| | | Aluminum in Samples Normalized to 2.5% Protein (ppb) | | |
|---|---|---|---|---|
| Albumin Preparation | DF pH | Clarified Fraction V Solution (SM) | Diafiltered Fraction V Solution (DS) | Final Container Albumin Solution (FS) |
| Example 5 | 6.2 | 6 | <5 | 7 |
| 20% Albumin | 8.8 | 6 | <5 | 16 |
| | 9.0 | 6 | <5 | <5 |
| | 9.2 | 6 | 24 | <5 |
| Example 6 | 6.2 | 13 | 44 | 9 |
| 25% Albumin | 9.0 | 13 | 37 | <5 |
| Lot One | 9.2 | 13 | 7 | <5 |
| Example 6 | 6.2 | 28 | 18 | 14 |
| 25% Albumin | 9.0 | 28 | 9 | 8 |
| Lot Two | 9.2 | 28 | <5 | <5 |

DF = diafiltration;
ppb = parts per billion.

TABLE 6

Citrate Test Results (Alpha Therapeutic Corporation)

| | | Citrate (ppm) | | |
|---|---|---|---|---|
| Albumin Preparation | DF pH | Clarified Fraction V Solution (SM) | Diafiltered Fraction V Solution (DS) | Final Container Albumin Solution (FS) |
| Example 5 | 6.2 | 3370 | 624 | 218 |
| 20% Albumin | 8.8 | 3370 | 41 | <29 |
| | 9.0 | 3370 | 32 | <29 |
| | 9.2 | 3370 | <29 | <29 |
| Example 6 | 6.2 | 1982 | 618 | 303 |
| 25% Albumin | 9.0 | 1982 | <29 | <29 |
| Lot One | 9.2 | 1982 | <29 | <29 |
| Example 6 | 6.2 | 2156 | 597 | 412 |
| 25% Albumin | 9.0 | 2156 | <29 | <29 |
| Lot Two | 9.2 | 2156 | <29 | <29 |

DF = diafiltration;
ppm = parts per million.
Citrate values in this table were measured at Alpha Therapeutics Corporation (ATC), Los Angeles, California.

TABLE 7

Citrate Test Results (West Coast Analytical Services)

| | | Citrate (ppm) | | |
|---|---|---|---|---|
| Albumin Preparation | DF pH | Clarified Fraction V Solution (SM) | Diafiltered Fraction V Solution (DS) | Final Container Albumin Solution (FS) |
| Example 5 | 6.2 | 1900 | 383 | 57 |
| 20% Albumin | 8.8 | 1900 | 15 | <2 |
| | 9.0 | 1900 | 12 | <2 |
| | 9.2 | 1900 | 6 | <2 |
| Example 6 | 6.2 | 1770 | 264 | 111 |
| 25% Albumin | 9.0 | 1770 | <2 | 8 |
| Lot One | 9.2 | 1770 | <2 | <2 |
| Example 6 | 6.2 | 1840 | 407 | 144 |

TABLE 7-continued

Citrate Test Results (West Coast Analytical Services)

|  |  | Citrate (ppm) | | |
|---|---|---|---|---|
| Albumin Preparation | DF pH | Clarified Fraction V Solution (SM) | Diafiltered Fraction V Solution (DS) | Final Container Albumin Solution (FS) |
| 25% Albumin Lot Two | 9.0 | 1840 | <2 | <2 |
|  | 9.2 | 1840 | <2 | <2 |

DF = diafiltration;
ppm = parts per million.
Citrate values in this table were determined at West Coast Analytical Services (WCAS).

As shown in Table 5, the concentration of aluminum after diafiltration at either pH 6.2, 8.8 or 9.0 decreased from 6 ppb in the clarified Fraction V solution to less than 5 ppb in the diafiltered sample (Example 5). Somewhat surprisingly, however, the concentration of aluminum apparently increased when diafiltered at pH 9.2, from 6 ppb in the SM to about 24 ppb in the DS. This result may be due to contamination of the aluminum assay. It should be noted that the final container (FS) of the albumin solution diafiltered at pH 9.2 was found to have an aluminum concentration of <5 ppb (Table 5). With the exception of the sample diafiltered at pH 8.8, aluminum concentration in the final containers showed a decreasing trend as the diafiltration pH was increased.

Similarly, results for 25% albumin solutions prepared as in Example 6 showed a decreasing concentration of aluminum as the diafiltration pH was increased. For example, the level of aluminum in albumin solutions following diafiltration at pH 6.2 was 44 ppb, decreasing to 37 ppb and 7 ppb at pH 9.0 and 9.2, respectively (Example 6, Lot One) or 18 ppb, decreasing to 9 ppb and <5 ppb at pH 9.0 and 9.2, respectively (Example 6, Lot Two).

As shown in Table 6, similar results were found for citrate levels in albumin solutions following diafiltration at higher pH values against deionized water. Diafiltration of clarified Fraction V solution (SM) at pH 6.2 reduced the amount of citrate from 3370 ppm to about 624 ppm (2.12 mM) (Example 5). Increasing the diafiltration pH to 8.8, 9.0 or 9.2 reduced the amount of citrate in the diafiltered sample (DS) to between 41 ppm (0.14 mM) and less than 29 ppm (<0.10 mM). Similar results were seen for solutions of 25% albumin prepared as in Example 6, where the level of citrate following diafiltration at pH 6.2 was 618 ppm (Lot One) and 597 (Lot Two), but dropped below the detection limit (less than 29 ppm or 0.10 mM) following diafiltration at pH 9.0 or 9.2 (Table 6). Similar results were found for samples sent to West Coast Analytical Services for testing (Table 7).

Figure 6:
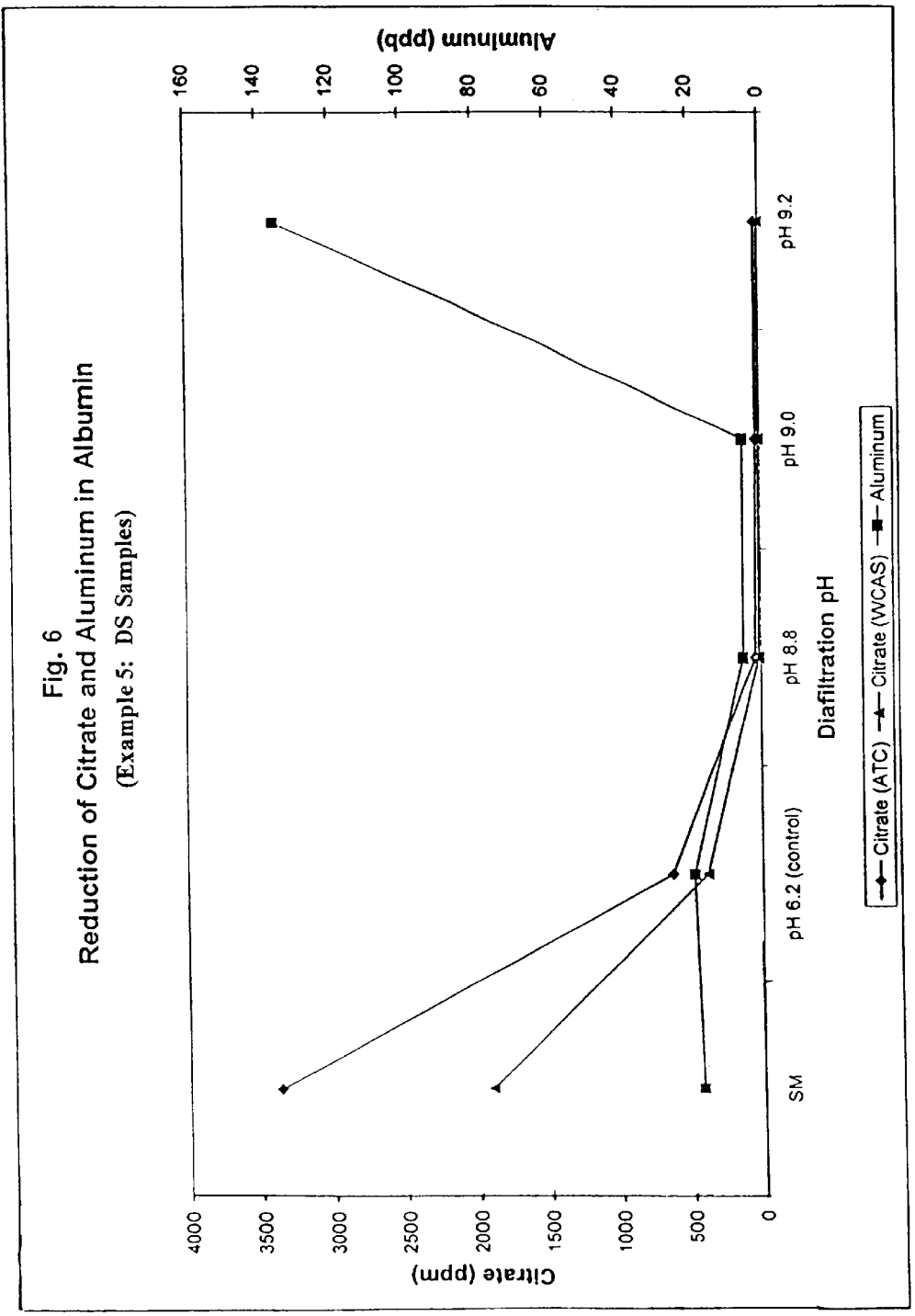
FIG. 6 is a graph illustrating the effect of diafiltration pH on the reduction of citrate and aluminum ions in clarified Fraction V solution, prepared as in Example 5, before and after diafiltration against deionized water.
Figure 7:
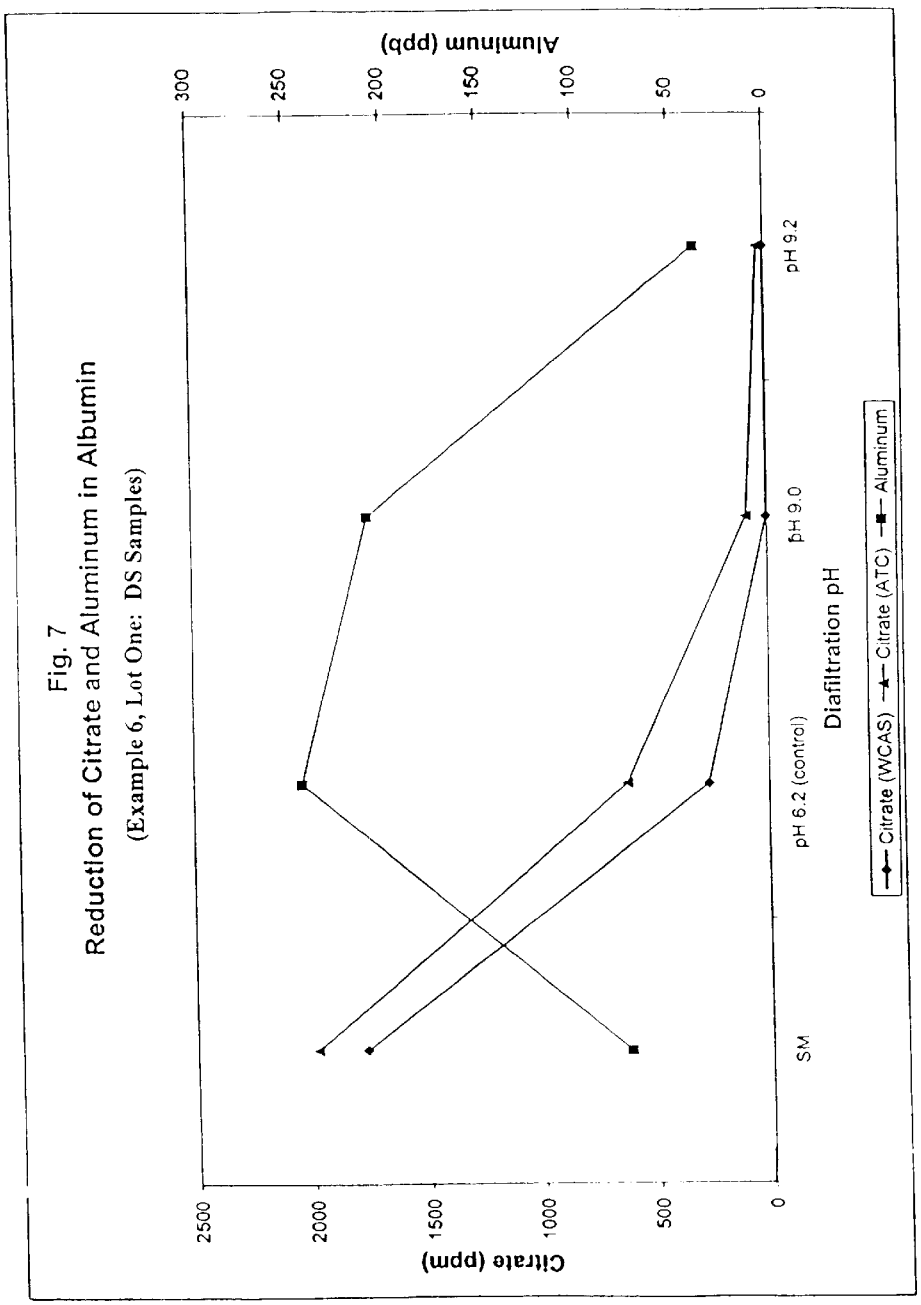
FIG. 7 is a graph illustrating the effect of diafiltration pH on the reduction of citrate and aluminum ions in clarified Fraction V solution, Lot One, prepared as in Example 6, before and after diafiltration against deionized water.
Figure 8:
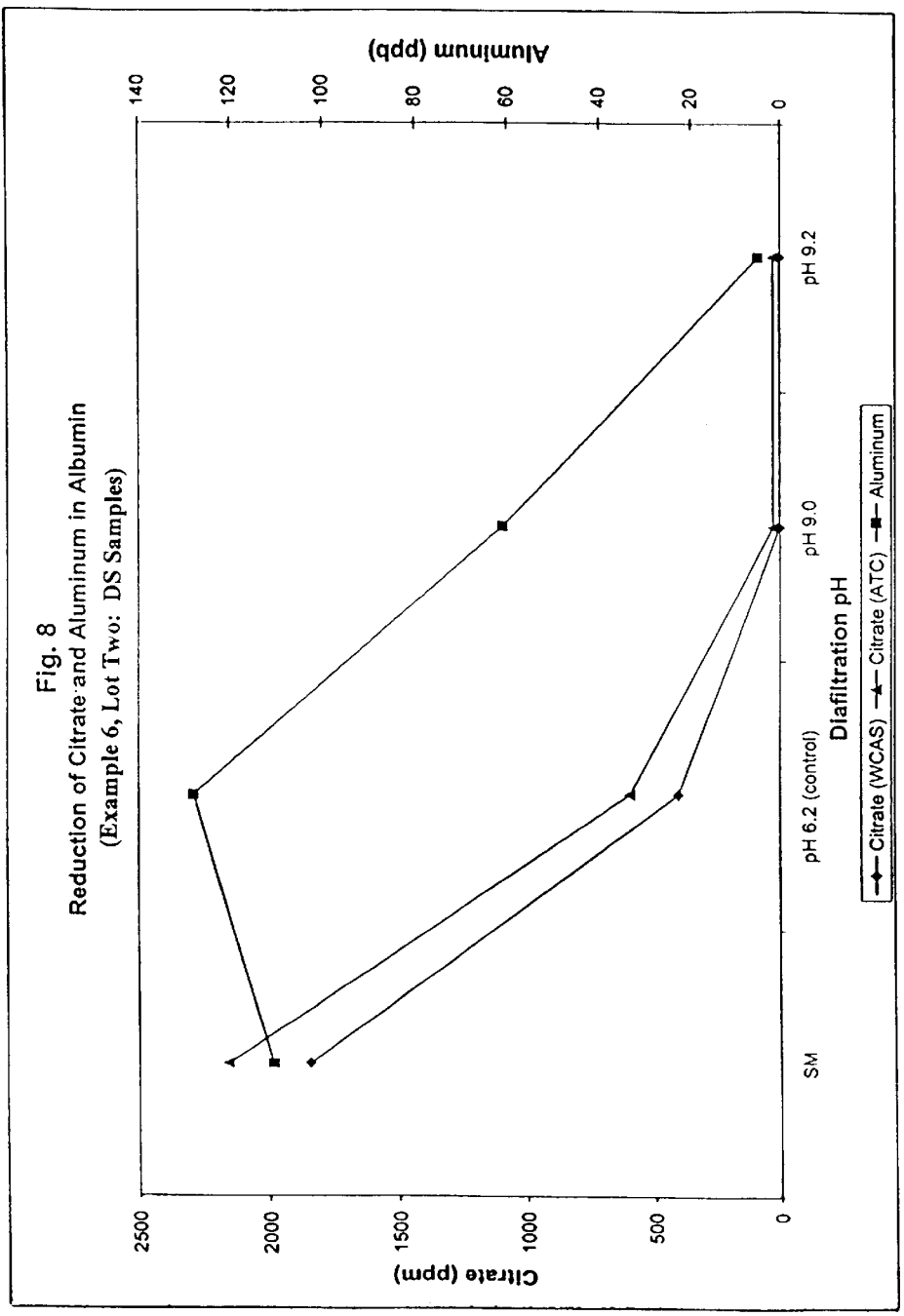
FIG. 8 is a graph illustrating the effect of diafiltration pH on the reduction of citrate and aluminum ions in clarified Fraction V solution, Lot Two, prepared as in Example 6, before and after diafiltration against deionized water.

The results of the aluminum and citrate assays for the starting material (SM) and diafiltered solutions (DS) are shown graphically in FIGS. 6 (20% Albumin, Example 5), 7 (25% Albumin, Lot One, Example 6) and 8 (25% Albumin, Lot Two, Example 6). Based on the results obtained before and after diafiltration of clarified Fraction V solutions during the preparation of 20% and 25% albumin solutions, it is apparent that the citrate and aluminum contents of the solutions decreased when the diafiltration pH was increased to 8.8, 9.0 or 9.2.

The citrate and aluminum results for the final container samples also demonstrate that increasing the diafiltration pH reduces levels of citrate and aluminum. The level of citrate in the final container samples was reduced below 29 ppm when the diafiltration pH was increased from pH 6.2 to pH 8.8, 9.0 or 9.2 (Table 6). The aluminum level for the final container solutions diafiltered at pH 9.0 or 9.2 were also lower compared to the corresponding control (diafiltered at pH 6.2) for each albumin preparation (Table 5). In all cases, the aluminum levels in the final containers after normalizing to 20% or 25% protein were within the specification of not more than 200 ppb aluminum. The results of the aluminum and citrate assays for the final container solutions (FS) are shown graphically in FIGS. 9 (20% Albumin, Example 5), 10 (25% Albumin, Lot One, Example 6) and 11 (25% Albumin, Lot Two, Example 6).

These results suggest that at a higher pH, the citrate binding to aluminum or proteins or both weakens and can be easily removed by diafiltration. This is consistent with Rabinow, B. E., Ericson, S., and Shelbourne, T. M. (1989) *J. Parenter. Sci. Technol.* 43: 132–139, who showed that at a higher pH (basic pH), the electrostatic attraction between citrate and aluminum weakens due to coulombic repulsion between the two species.

EXAMPLE 9

Purity, Clarity, Acetone Content and HPSEC Results Before and After Diafiltration of Clarified Fraction V and in Final Container Solutions of 20% and 25% Albumin While increasing the diafiltration pH results in lower levels of citrate and aluminum, it is important to ensure that the higher diafiltration pH does not adversely affect other physical properties of the albumin solutions. Most commercial albumin solutions, for example, must conform to predetermined specifications for a variety of physical characteristics. For example, a typical specification for commercial albumin solutions includes the following requirements: an aluminum content of not more than 200 ppb, a purity of not less than 96% albumin, an acetone content of not more than 0.02 g/100 mL, and a molecular size distribution of not less than 80% monomer and not more than 9%, 15% and 6% for dimer, polymer, and fragments, respectively. Accordingly, these physical characteristics were measured in SM, DS, and FS samples from all three albumin preparations described in Examples 5 and 6.

The purity of clarified Fraction V solutions before and after diafiltration at different pH values and in the final container solutions was determined by cellulose acetate membrane electrophoresis (CAME). The results are shown in Table 8.

TABLE 8

CAME Test Results

|  |  | Albumin (%)* | | |
|---|---|---|---|---|
| Albumin Preparation | DF pH | Clarified Fraction V Solution (SM) | Diafiltered Fraction V Solution (DS) | Final Container Albumin Solution (FS) |
| Example 5 | 6.2 | 99.1 | 99.0 | 99.8 |
| 20% Albumin | 8.8 | 99.1 | 99.6 | 99.8 |
|  | 9.0 | 99.1 | 99.5 | 99.1 |
|  | 9.2 | 99.1 | 99.6 | 99.7 |
| Example 6 | 6.2 | 99.0 | 99.4 | 99.9 |
| 25% Albumin | 9.0 | 99.0 | 99.4 | 99.9 |

TABLE 8-continued

CAME Test Results

Albumin (%)*

| Albumin Preparation | DF pH | Clarified Fraction V Solution (SM) | Diafiltered Fraction V Solution (DS) | Final Container Albumin Solution (FS) |
|---|---|---|---|---|
| Lot One | 9.2 | 99.0 | 99.1 | 99.8 |
| Example 6 | 6.2 | 99.2 | 99.4 | 98.9 |
| 25% Albumin | 9.0 | 99.2 | 99.3 | 99.2 |
| Lot Two | 9.2 | 99.2 | 99.8 | 99.2 |

DF = diafiltration.
*Albumin (%) refers to the amount of albumin relative to the total protein present in the sample as measured by CAME.

As shown in Table 8, the purity of the albumin solution in all three preparations ranged from 99.0% to 99.2% before diafiltration and from 99.0% to 99.8% after diafiltration. The purity of all the final container solutions ranged from 98.9% to 99.9% albumin, well within the specification of not less than 96% albumin.

The clarity of the albumin solutions before and after diafiltration and in final container solutions was measured by nephelometry using a 12×75 mm tube. The results are shown in Table 9.

TABLE 9

Nephelometry Test Results

Clarity (NTU)

| Albumin Preparation | DF pH | Clarified Fraction V Solution (SM) | Diafiltered Fraction V Solution (DS) | Final Container Albumin Solution (FS) |
|---|---|---|---|---|
| Example 5 | 6.2 | 2.0 | 3.5 | 2.1 |
| 20% Albumin | 8.8 | 2.0 | 1.6 | 2.6 |
|  | 9.0 | 2.0 | 1.4 | 2.4 |
|  | 9.2 | 2.0 | 1.2 | 2.4 |
| Example 6 | 6.2 | 2.0 | 3.6 | 1.9 |
| 25% Albumin | 9.0 | 2.0 | 2.4 | 2.1 |
| Lot One | 9.2 | 2.0 | 2.4 | 1.8 |
| Example 6 | 6.2 | 2.2 | 4.3 | 1.9 |
| 25% Albumin | 9.0 | 2.2 | 2.4 | 1.6 |
| Lot Two | 9.2 | 2.2 | 2.2 | 1.8 |

DF = diafiltration;
NTU = nephelometric turbidity unit.

The clarity of the clarified Fraction V solutions before diafiltration ranged from 2.0 NTU to 2.2 NTU in all three preparations. There was an increase in the nephelometry reading, which is an indication of turbidity, after diafiltration at pH 6.2. When the diafiltration pH was increased to pH 8.8, 9.0 or 9.2, the clarity either improved slightly or remained almost the same. The clarity of all the final container solutions were in the range of 1.6 NTU to 2.6 NTU.

The acetone content of the albumin solutions before and after diafiltration and in final container solutions is shown in Table 10.

TABLE 10

Acetone Test Results

Acetone (g/100 mL)

| Albumin Preparation | DF pH | Clarified Fraction V Solution (SM) | Diafiltered Fraction V Solution (DS) | Final Container Albumin Solution (FS) |
|---|---|---|---|---|
| Example 5 | 6.2 | 0.010 | 0.001 | 0.001 |
| 20% Albumin | 8.8 | 0.010 | 0.004 | 0.001 |
|  | 9.0 | 0.010 | 0.002 | 0.001 |
|  | 9.2 | 0.010 | 0.002 | 0.001 |
| Example 6 | 6.2 | 0.003 | 0.001 | 0.001 |
| 25% Albumin | 9.0 | 0.003 | 0.001 | 0.001 |
| Lot One | 9.2 | 0.003 | 0.001 | 0.001 |
| Example 6 | 6.2 | 0.006 | 0.001 | 0.002 |
| 25% Albumin | 9.0 | 0.006 | 0.002 | 0.002 |
| Lot Two | 9.2 | 0.006 | 0.001 | 0.002 |

DF = diafiltration.

Before diafiltration, the acetone content ranged from 0.003 to 0.010 g/100 mL for all three preparations of albumin. The acetone level decreased to a range of 0.001 to 0.004 g/100 mL after diafiltration and did not seem to be affected by the diafiltration pH. Although the starting level of acetone was low, the decrease in the amount of acetone after diafiltration indicates that acetone was further removed during the process. The acetone content of all the final container solutions ranged from 0.001 to 0.002 g/100 mL, which is well within a specification of not more than 0.02 g/100 mL.

The molecular distribution of albumin, determined by High Performance Size Exclusion Chromatography (HPSEC) before and after diafiltration and in the final container solutions is given in Tables 11, 12 and 13 for the three albumin preparations described in Examples 5 and 6.

TABLE 11

Molecular Distribution by HPSEC (Example 5:20% Albumin)

| DF pH | Molecular Size (%) | Clarified Fraction V Solution (SM) | Diafiltered Fraction V Solution (DS) | Final Container Albumin Solution (FS) |
|---|---|---|---|---|
| 6.2 | Monomer | 94.3 | 92.9 | 88.3 |
|  | Dimer | 4.0 | 5.4 | 2.4 |
|  | Polymer | 0.9 | 1.3 | 8.6 |
|  | Fragments | 0.8 | 0.4 | 0.7 |
| 8.8 | Monomer | 94.3 | 93.7 | 87.2 |
|  | Dimer | 4.0 | 3.9 | 3.2 |
|  | Polymer | 0.9 | 1.3 | 9.1 |
|  | Fragments | 0.8 | 1.1 | 0.5 |
| 9.0 | Monomer | 94.3 | 94.9 | 87.5 |
|  | Dimer | 4.0 | 3.4 | 2.8 |
|  | Polymer | 0.9 | 1.0 | 8.9 |
|  | Fragments | 0.8 | 0.7 | 0.8 |
| 9.2 | Monomer | 94.3 | 94.3 | 87.3 |
|  | Dimer | 4.0 | 4.0 | 2.8 |
|  | Polymer | 0.9 | 1.0 | 9.2 |
|  | Fragments | 0.8 | 0.7 | 0.7 |

DF = Diafiltration; polymer = greater than a dimer.

TABLE 12

Molecular Distribution by HPSEC
(Example 6: 25% Albumin, Lot One)

| DF pH | Molecular Size (%) | Clarified Fraction V Solution (SM) | Diafiltered Fraction V Solution (DS) | Final Container Albumin Solution (FS) |
|---|---|---|---|---|
| 6.2 | Monomer | 92.3 | 92.2 | 87.3 |
|  | Dimer | 5.2 | 6.0 | 3.4 |
|  | Polymer | 0.6 | 1.3 | 8.9 |
|  | Fragments | 1.9 | 0.5 | 0.4 |
| 9.0 | Monomer | 92.3 | 93.5 | 87.8 |
|  | Dimer | 5.2 | 5.1 | 2.7 |
|  | Polymer | 0.6 | 0.9 | 8.7 |
|  | Fragments | 1.9 | 0.05 | 0.8 |
| 9.2 | Monomer | 92.3 | 92.4 | 87.4 |
|  | Dimer | 5.2 | 5.4 | 3.2 |
|  | Polymer | 0.6 | 1.0 | 8.9 |
|  | Fragments | 1.9 | 1.2 | 0.5 |

DF = diafiltration; polymer = greater than a dimer.

TABLE 13

Molecular Distribution by HPSEC
(Example 6: 25% Albumin, Lot Two)

| DF pH | Molecular Size (%) | Clarified Fraction V Solution (SM) | Diafiltered Fraction V Solution (DS) | Final Container Albumin Solution (FS) |
|---|---|---|---|---|
| 6.2 | Monomer | 88.1 | 93.5 | 88.7 |
|  | Dimer | 8.8 | 4.8 | 2.3 |
|  | Polymer | 0.9 | 0.6 | 8.3 |
|  | Fragments | 2.2 | 1.1 | 0.7 |
| 9.0 | Monomer | 88.1 | 94.1 | 89.3 |
|  | Dimer | 8.8 | 4.1 | 2.1 |
|  | Polymer | 0.9 | 1.0 | 8.3 |
|  | Fragments | 2.2 | 0.8 | 0.3 |
| 9.2 | Monomer | 88.1 | 93.9 | 87.8 |
|  | Dimer | 8.8 | 4.8 | 2.5 |
|  | Polymer | 0.9 | 0.7 | 8.9 |
|  | Fragments | 2.2 | 0.6 | 0.8 |

DF = diafiltration; polymer = greater than a dimer.

As shown in Tables 11, 12 and 13, the amount of monomer before diafiltration ranged from 88.1% to 94.3%, the amount of dimer ranged from 4.0% to 8.8%, the amount of polymer ranged from 0.6% to 0.9% and the amount of fragments ranged from 0.8% to 2.2%. After diafiltration, the amount of monomer ranged from 92.2% to 94.9%, the amount of dimer ranged from 3.4% to 6.0%, the amount of polymer ranged from 0.6% to 1.3% and the amount of fragments ranged from less than 0.4% to 1.2%. The amount of monomer in the final container solutions ranged from 87.2% to 89.3%, all within the specification of not less than 80%. Likewise, the amount of dimer, polymer and fragments were all within specified ranges (not more than 9%, 15%, and 6%, respectively).

Although there was a great deal of variation in the relative amount of monomer, dimer, polymer and fragments between the three preparations, within each preparation the variation was not significant.

EXAMPLE 10

Protein Secondary Structure in Final Container Solutions of 20% and 25% Albumin

An overlay plot (FIG. 12) of the circular dichroism (CD) spectra of all the final containers of albumin solution shows that the structure of the protein contained in the samples is qualitatively very similar. The CD tests were performed by Common Wealth Biotechnologies, Inc. (Richmond, Va.).

EXAMPLE 11

Differential Scanning Calorimetry (DSC) Results of Final Container Solutions of 20% and 25% Albumin The DSC results of the albumin final container solutions are summarized in Table 14. The melting temperature, molar heat (H) and Van't Hoff heat changes (Hv) of the control (diafiltration pH 6.2) and the samples (diafiltration pH 8.8, 9.0 and 9.2) were within ±2 SD of the average. These data indicate that there is no significant difference in the secondary protein structure among the final container samples from all 3 lots prepared as in Examples 5 and 6. The DSC tests were also performed by Common Wealth Biotechnologies, Inc. (Richmond, Va.).

TABLE 14

Differential Scanning Calorimetry Results
of Albumin Final Container Solutions

| Sample | Diafiltration pH | Melting Temp. °C. | Molar Heat, H (cal/mol) | Vhoff, Hv (cal/mol) |
|---|---|---|---|---|
| Example 5 | 6.2 | 66.27 | 2.29E+05 | 9.88E+04 |
| 20% Albumin | 8.8 | 67.17 | 2.39E+05 | 9.91E+04 |
|  | 9.0 | 67.40 | 2.59E+05 | 1.03E+05 |
|  | 9.2 | 67.52 | 2.30E+05 | 1.04E+05 |
| Example 6 | 6.2 | 66.38 | 2.28E+05 | 9.53E+04 |
| 25% Albumin | 9.0 | 66.51 | 2.24E+05 | 9.38E+04 |
| Lot One | 9.2 | 66.38 | 2.37E+05 | 9.27E+04 |
| Example 6 | 6.2 | 66.61 | 2.34E+05 | 1.02E+05 |
| 25% Albumin | 9.0 | 66.08 | 2.42E+05 | 9.79E+04 |
| Lot Two | 9.2 | 66.80 | 2.39E+05 | 9.97E+04 |
| Average | Not applicable | 66.76 | 2.37E+05 | 9.86E+04 |
| Std. Dev. | Not applicable | 0.50 | 9.89 + 03 | 3.81E+03 |

EXAMPLE 12

Total Protein, Heat Stability and Appearance of Final Container Solutions of 20% and 25% Albumin The total protein concentrations in the final container solutions (FS) of 20% and 25% albumin prepared as described in Examples 5 and 6 are shown in Table 15. A typical specification for commercial albumin solutions has the following concentration requirements: a total protein concentration of 18.8 to 21.2 g/100 mL (for 20% albumin) or 23.5 to 26.5 g/100 mL (for 25% albumin)

TABLE 15

Protein Concentrations in Final Container
Solutions of 20% and 25% Albumin

| Albumin Preparation | DF pH | Total Protein (g/100 mL) |
|---|---|---|
| 20% Albumin | 6.2 | 20.5 |
| (Example 5) | 8.8 | 19.9 |
|  | 9.0 | 19.6 |
|  | 9.2 | 19.0 |
| 25% Albumin | 6.2 | 23.9 |
| Lot One | 9.0 | 23.5 |

TABLE 15-continued

Protein Concentrations in Final Container Solutions of 20% and 25% Albumin

| Albumin Preparation | DF pH | Total Protein (g/100 mL) |
|---|---|---|
| (Example 6) | 9.2 | 24.1 |
| 25% Albumin | 6.2 | 27.3 |
| Lot Two | 9.0 | 23.5 |
| (Example 6) | 9.2 | 23.5 |

As shown in Table 15, the protein concentration of the final containers of 20% albumin ranged from 19.0 to 20.5 g/100 mL, well within the specification of 18.8 to 21.2 g/100 mL. Likewise, the protein concentration for the final containers of 25% albumin, Lot One, ranged from 23.5 to 24.1 g/100 mL, which were all within the specification of 23.5 to 26.5 g/100 mL. One of the three final containers in Lot Two (25% albumin) had a protein concentration of 27.3 g/100 mL, which is about 0.8 g/100 mL higher than the specification. The small difference in the protein concentration, however, should not have an adverse impact on the quality of the final container albumin product or the level of aluminum in the product.

The results of the heat stability study (shown in Table 16) demonstrate that 20% and 25% albumin prepared as in Examples 5 and 6 at various diafiltration pH values are all within the specified levels (visually clear, before and after heating, and not more than 16 NTU in the control or 21 NTU in the sample.)

TABLE 16

Heat Stability of Albumin Final Container Solutions

| Albumin Prep. | DF pH | Visual Pre-heating Control | Visual Pre-heating Sample | Visual Post heating Control | Visual Post heating Sample | Clarity (NTU)* Pre-heating Control | Clarity (NTU)* Post heating Sample |
|---|---|---|---|---|---|---|---|
| 20% Albumin Example 5 | 6.2 | clear | clear | not heated | clear | 6.0 | 7.0 |
|  | 8.8 | clear | clear | not heated | clear | 6.4 | 7.2 |
|  | 9.0 | clear | clear | not heated | clear | 6.0 | 6.9 |
|  | 9.2 | clear | clear | not heated | clear | 6.1 | 7.0 |
| 25% Albumin Lot One Example 6 | 6.2 | clear | clear | not heated | clear | 4.8 | 5.7 |
|  | 9.0 | clear | clear | not heated | clear | 5.1 | 5.8 |
|  | 9.2 | clear | clear | not heated | clear | 5.4 | 6.5 |
| 25% Albumin Lot Two Example 6 | 6.2 | clear | clear | not heated | clear | 4.4 | 5.0 |
|  | 9.0 | clear | clear | not heated | clear | 4.2 | 5.1 |
|  | 9.2 | clear | clear | not heated | clear | 4.5 | 5.3 |

*Turbidity was measured using a 30-mL Hach ratio sample cell

Finally, all of the final container solutions were visually inspected to determine if the appearance of the albumin products diafiltered at higher pH values were within commercial specifications, requiring a clear, slightly viscous, green or amber to straw-colored solution of varying intensity. All of the final container samples were found to be clear, amber and slightly viscous, well within specification parameters.

Diafiltration of clarified Fraction V solutions at pH values ranging from 8.8 to 9.2 reduced the citrate content of the final albumin solutions to below the detection limit (29 ppm or 0.10 mM), and reduced the level of aluminum, without significantly altering the measurable properties of final albumin solutions.

As can be seen from the above examples, diafiltration of pH-adjusted protein solutions against pure water is a simple and effective method for removing citrate and aluminum ions. By adjusting the pH of the protein solution above about 7 and diafiltering against pure water, multivalent ions, as well as monovalent ions, salts, solvents and other small molecular weight molecules, can be removed from proteins at the same time.

The above descriptions of exemplary embodiments of methods for removing contaminants from protein solutions are illustrative of the present invention. Because of the variations, which will be apparent to those skilled in the art, however, the present invention is not intended to be limited to the particular embodiments described above. The scope of the invention is defined in the following claims.

What is claimed is:

1. A method for removing multivalent ions from a protein, the method comprising the steps of:
   providing an aqueous solution comprising a protein and multivalent ions;
   adjusting the aqueous solution to a pH from about 7 to about 10; and
   diafiltering the aqueous solution against pure water to thereby provide a filtrate comprising the multivalent ions and a retentate comprising the protein.

2. The method of claim 1, wherein the multivalent ions are at least one from the group consisting of aluminum and citrate.

3. The method of claim 1, wherein the protein is selected from the group consisting of albumin, immunoglobulin, Factor VIII, Factor IX, alpha-1-proteinase inhibitor, and prothrombin complex.

4. The method of claim 1, wherein the aqueous solution is diafiltered against pure water in an amount equal to at least three times the volume of the aqueous solution.

5. The method of claim 4, wherein the aqueous solution is diafiltered against pure water in an amount equal to at least five times the volume of the aqueous solution.

6. The method of claim 1, wherein the aqueous solution is diafiltered against pure water in an amount equal to at least three times the weight of the aqueous solution.

7. The method of claim 6, wherein the aqueous solution is diafiltered against pure water in an amount equal to at least five times the weight of the aqueous solution.

8. The method of claim 1, wherein the aqueous solution is adjusted to a pH from about 8.5 to about 9.5.

9. The method of claim 8, wherein the aqueous solution is adjusted to a pH from about 8.8 to about 9.2.

10. The method of claim 1, wherein the aqueous solution is solubilized Cohn Fraction V.

11. A method for removing multivalent ions from a protein, the method comprising the steps of:
   introducing an aqueous solution comprising a protein and multivalent ions into a source tank, wherein the aqueous solution is adjusted to a pH from about 7 to about 10;
   pumping the aqueous solution from the source tank through a diafiltration device to thereby produce a retentate comprising the protein and a filtrate comprising the multivalent ions, wherein the filtrate is removed from the diafiltration device;

transporting the retentate to the source tank;

adding pure water to the retentate in the source tank to thereby provide a diluted retentate; and repeating the steps of pumping the diluted retentate from the source tank, through the diafiltration device, back to the source tank, and adding pure water until the multivalent ions are removed from the protein.

12. The method of claim 11, wherein the multivalent ions are selected from the group consisting of aluminum, citrate, and mixtures thereof.

13. The method of claim 11, wherein the protein is selected from the group consisting of albumin, immunoglobulin, Factor VIII, Factor IX, alpha-1-proteinase inhibitor, and prothrombin complex.

14. The method of claim 11, wherein the protein is albumin and the multivalent ions are citrate.

15. The method of claim 11, wherein the protein is albumin and the multivalent ions are aluminum.

16. The method of claim 11, wherein the pure water is added in an amount equal to at least three times the volume of the aqueous solution.

17. The method of claim 16, wherein the pure water is added in an amount equal to at least five times the volume of the aqueous solution.

18. The method of claim 11, wherein the pure water is added in an amount equal to at least three times the weight of the aqueous solution.

19. The method of claim 18, wherein the pure water is added in an amount equal to at least five times the weight of the aqueous solution.

20. The method of claim 11, wherein the pure water is added continuously so as to maintain a constant volume in the source tank.

21. The method of claim 11, wherein the aqueous solution is adjusted to a pH from about 8.8 to about 9.2.

22. A method for removing citrate ions from albumin, the method comprising the steps of:

providing an aqueous solution comprising albumin and citrate ions;

adjusting the pH of the aqueous solution to a pH from about 7.0 to about 10.0; and diafiltering the pH-adjusted aqueous solution against pure water to thereby provide a retentate comprising albumin and a filtrate comprising citrate ions.

23. The method of claim 22, wherein the aqueous solution is solubilized Cohn Fraction V.

24. The method of claim 22, wherein the aqueous solution is adjusted to a pH from about 8.5 to about 9.5.

25. The method of claim 24, wherein the aqueous solution is adjusted to a pH from about 8.8 to about 9.2.

26. The method of claim 22, wherein the pH-adjusted aqueous solution is diafiltered against pure water in an amount equal to at least five times the weight of the aqueous solution.

27. The method of claim 22, wherein the pH-adjusted aqueous solution is diafiltered against pure water in an amount equal to at least five times the volume of the aqueous solution.

28. A method for removing aluminum ions from albumin, the method comprising the steps of:

providing an aqueous solution comprising albumin and aluminum ions;

adjusting the aqueous solution to a pH from about 7.0 to about 10.0; and diafiltering the pH-adjusted aqueous solution against pure water to thereby provide a retentate comprising albumin and a filtrate comprising aluminum ions.

29. The method of claim 28, wherein the aqueous solution is solubilized Cohn Fraction V.

30. The method of claim 28, wherein the aqueous solution is adjusted to a pH from about 8.5 to about 9.5.

31. The method of claim 30, wherein the aqueous solution is adjusted to a pH from about 8.8 to about 9.2.

32. The method of claim 28, wherein the pH-adjusted aqueous solution is diafiltered against pure water in an amount equal to at least five times the weight of the aqueous solution.

33. The method of claim 28, wherein the pH-adjusted aqueous solution is diafiltered against pure water in an amount equal to at least five times the volume of the aqueous solution.

* * * * *